United States Patent [19]

Chakerian et al.

[11] Plant 4,570

[45] Jul. 15, 1980

[54] NECTARINE TREE

[75] Inventors: Jonathan P. Chakerian; Dennis G. Surabian, both of Reedley, Calif.

[73] Assignee: Surabian Brothers, Reedley, Calif.

[21] Appl. No.: 14,740

[22] Filed: Feb. 23, 1979

[51] Int. Cl.[3] ..... A01H 5/03
[52] U.S. Cl. ..... Plt./41
[58] Field of Search ..... Plt./41

[56] References Cited

U.S. PATENT DOCUMENTS

P.P. 4,084 7/1977 Parnagian ..... Plt./41

*Primary Examiner*—Robert E. Bagwill
*Attorney, Agent, or Firm*—Huebner & Worrel

[57] ABSTRACT

A nectarine tree, generally similar to the Armking Nectarine Tree (U.S. Plant Pat. No. 2,943) which it most nearly resembles, bearing yellow fleshed, semi-freestone fruit of large size for its ripening season which is from five to seven days earlier than the Armking.

4 Drawing Figures

BACKGROUND OF THE VARIETY

The present invention relates to a new and distinct variety of nectarine tree which is generally similar to the Armking Nectarine Tree (U.S. Plant Pat. No. 2,943), of which it is a sport, but which bears fruit which is firmer and more rounded than the Armking and which ripens five to seven days earlier.

The Armking Nectarine Tree is well suited for commercial planting and is well known as a vigorous and productive bearer of yellow fleshed, semi-freestone nectarines of medium to large size for their ripening season. However, its ripening date of seven to nine days after other varieties, such as the Mayred Nectarine Tree (U.S. Plant Pat. No. 2,758), is disadvantageous despite its fruit being of larger size than the fruit of such varieties. It has been recognized as highly desirable to provide a nectarine tree bearing fruit which can be marketed at the same time as the Mayred but which is of larger size and of equal or superior quality.

ORIGIN AND ASEXUAL REPRODUCTION OF THE NEW VARIETY

The new variety of nectarine tree was discovered by Jonathan P. Chakerian on May 26, 1976 as a sport growing in an orchard of Armking Nectarine Trees owned and farmed by Dennis Surabian of Reedley, Calif. by whom Chakerian is employed and whose duties include the care and maintenance of such orchard at the southeast corner of Alta and Huntsman Avenues, near the City of Reedley, in the County of Fresno, in the State of California.

The sport was asexually reproduced by Dennis Surabian by grafting on a farm operated by him and owned by a trust of which he is a trustee. The farm is located on the southeast corner of Sumner and Frankwood Avenues, near the City of Reedley, in the County of Fresno, in the State of California. The fruit and tree characteristics resulting from such grafting proved identical to those of the original sport.

SUMMARY OF THE NEW VARIETY

The instant variety of nectarine tree is characterized by perpetuating the general characteristics of the Armking Nectarine Tree, but has the important distinction of bearing fruit which ripens from five to seven days earlier. The fruit borne by the instant variety is also more globose and firmer fleshed than that borne by the Armking Tree. The new nectarine tree bears fruit of large size for its ripening season. For example, under similar growing conditions fruit of the nectarine tree of the present variety had an average axial diameter of 2 3/16 inches (55.5 mm). The axial diameter of fruit ripening at substantially the same time of the Mayred Nectarine Tree (U.S. Plant Pat. No. 2,758) was 1 15/16 inch (49 mm).

BRIEF DESCRIPTION OF THE DRAWINGS

The accompanying drawing is a color photograph of mature nectarines of the subject variety, two thereof showing the flesh color along the suture plane, together with a typical twig showing characteristic leaves.

DETAILED DESCRIPTION

Referring more specifically to the pomological details of this new and distinct variety of nectarine tree, the following has been observed under the ecological conditions prevailing in the designated orchards near Reedley, Calif. All major color code plate identifications are by reference to the Nickerson Color Fan of the American Horticultural Council.

TREE

Size: Large.
Productivity: Good.
Leaves:

*Length.*—165 mm. average.
*Width.*—41 mm. average.
*Shape.*—Lanceolate, apex acuminate.
*Color.*—Upperside moderate olive green (7.5 GY 4/4), underside moderate yellow green (2.5 GY 5/5).
*Marginal form.*—Serrulate.
*Petiole.*—Length 9 mm., thickness 2 mm.
*Glandular characteristics.*—Two to four, irregularly arranged on petiole and base of the blade, globose to slightly reniform, ½ to 1 mm. in width, dark greenish yellow (10 Y 6/7).
*Stipules.*—Often exstipulate; when present, ½ to 1 mm. wide and length 13 mm. average.

Flowers: Similar to Armking (U.S. Plant Pat. No. 2,943).

FRUIT

Maturity: Five to seven days before Armking. Five to seven days later than fruit of the nectarine tree of U.S. Plant Pat. No. 4,084. In 1977, May 21 to 30; in 1978, May 12 to 24.

Size: Large for ripening season.

*Average dimensions when girdled.*—Axial diameter — 57 mm. Transverse in suture plane — 55 mm. Transverse at right angles to suture plane — 48 mm.

Form: Irregular and asymetric.

*Suture.*—Ventral side only, from apex to stem cavity, often streaked with base color.

*Ventral surface.*—Lips unequal.

*Stem cavity.*—Rounded, 20 mm., diameter average.

*Pistil point.*—Slight.

Stem: Caliper — 3 to 4 mm.

Skin: Tendency to crack — slight.

*Pubescence.*—None.

*Color.*—Background strong greenish yellow (10 Y 7/9); mottled to approximately two-thirds solid, especially at apex, with dark red (5 R 3/7).

Flesh:

*Color.*—Uniform including surface of pit cavity, brilliant yellow (2.5 Y 9/9) to vivid yellow (2.5 Y 8/12). Firmer than flesh of Armking Nectarine Tree.

Stone: Semi-freestone.

*Size.*—Axial length: 35 mm. average. Width in suture plane: 25 mm. average. Width at right angles to suture plane: 19 mm. average.

*Form.*—Oval.

*Ventral edge.*—No wing, grooves unsymmetrical with one very deep.

*Dorsal edge.*—No wing, groove from base three-fourths to entirely from base to apex.

*Color.*—Pale yellow orange (7.5 YR 9/4).

It will be noted in the drawing that the stones exposed by division of the nectarines along the suture plane are immature or underdeveloped. This is believed characteristic of girdled nectarines and is a result of cultural practices, as in other varieties of nectarines, rather than a varietal characteristic unique to the subject variety.

As compared with the nectarine tree of U.S. Plant Pat. No. 4,084 grown under similar environmental conditions and cultural practices, the subject variety bears fruit which ripens five to seven days later, which fruit is semi-freestone rather than clingstone, is somewhat more endwardly tapered, and has a transverse diameter at right angles to its suture plane substantially less than its axial diameter or transverse diameter in the suture plane, as contrasted with the nearly equal corresponding diameters in the fruit of the nectarine tree of the designated patent. Further, the flavor of the fruit of these two varieties is good but distinctive from each other and the skin of the fruit of the subject variety is minutely speckled.

Although the new variety of nectarine tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated our new variety of nectarine tree, what is new and desired to be secured by Letters Patent is:

1. A new and distinct variety of nectarine tree, substantially as illustrated and described, characterized by its bearing of semi-freestone, yellow fleshed fruit which is of large size for its relatively early ripening season; and by its general resemblance to the Armking Nectarine Tree (U.S. Plant Pat. No. 2,943), which it most nearly resembles, but from which it is distinguished by its fruit ripening from five to seven days earlier, having firmer flesh, and being more rounded.

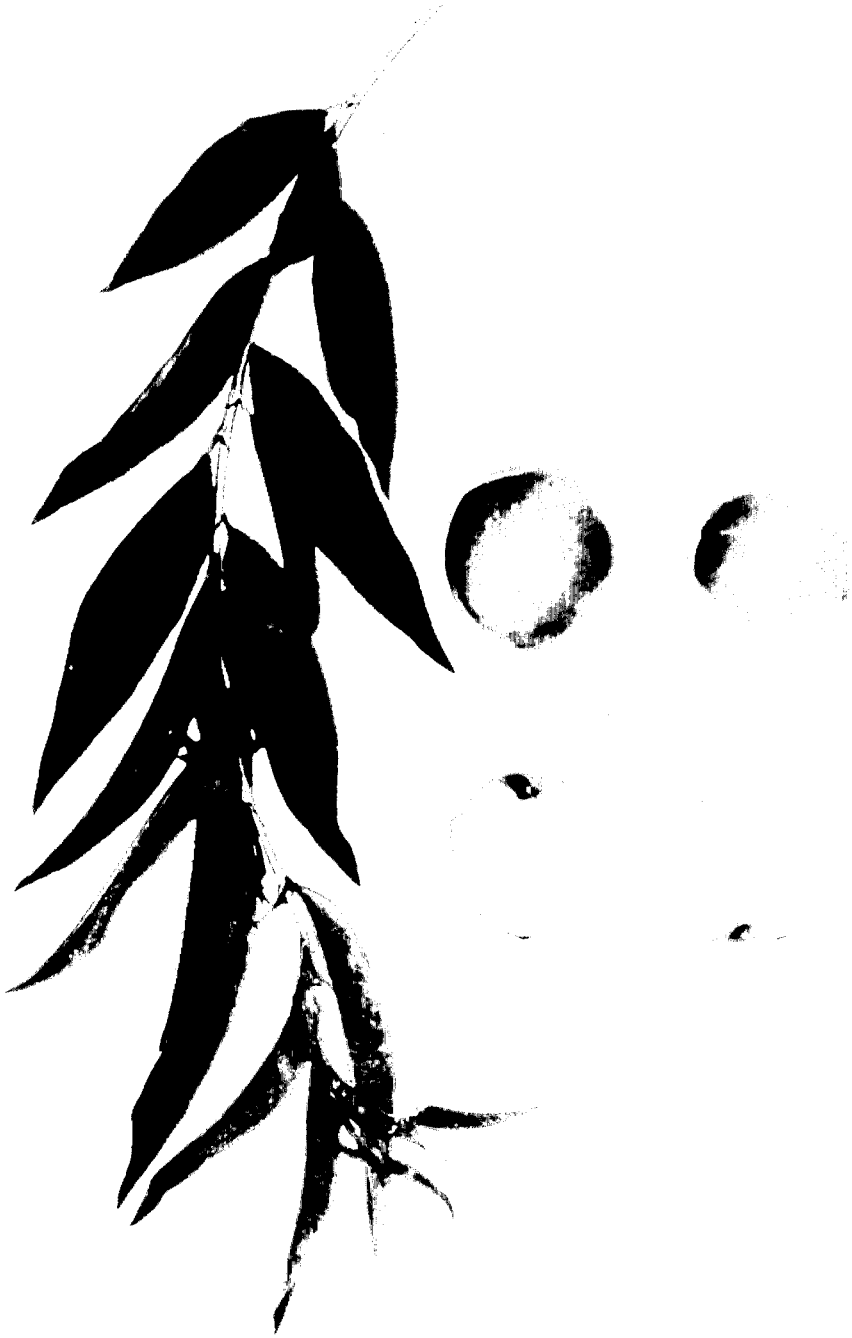

* * * * *